United States Patent [19]

Virgilio et al.

[11] Patent Number: 5,436,338
[45] Date of Patent: Jul. 25, 1995

[54] HETEROCYCLIC FORMAMIDINES USEFUL AS ULTRAVIOLET LIGHT ABSORBERS

[75] Inventors: Joseph A. Virgilio, Wayne; Emanuel Heilweil, Fairfield, both of N.J.; Isaac D. Cohen, Brooklyn, N.Y.

[73] Assignee: Givaudan-Roure Corporation, Clifton, N.J.

[21] Appl. No.: 45,571

[22] Filed: Apr. 9, 1993

Related U.S. Application Data

[62] Division of Ser. No. 630,467, Dec. 19, 1990, Pat. No. 5,243,055.

[51] Int. Cl.⁶ .................................. C07D 277/38
[52] U.S. Cl. ................................ 544/330; 546/163; 546/304; 252/401; 252/405
[58] Field of Search ................ 546/304, 163, 306; 544/330; 252/401, 405

[56] References Cited

U.S. PATENT DOCUMENTS

| | | | |
|---|---|---|---|
| 2,843,595 | 7/1958 | Engelhard | 546/304 |
| 4,021,471 | 5/1977 | Virgilio et al. | 546/304 |
| 4,535,088 | 8/1985 | Makisumi et al. | 514/370 |
| 4,699,915 | 10/1987 | Cereda et al. | 514/357 |

OTHER PUBLICATIONS

Lorenz et al, Journal of Organic Chemistry, vol. 30, 2531–2533, Aug. 1965.
Chemical Abstracts 106: 50,190 Abstract of Jpn. Kokai Tokyo Koho JP 61/68,478 8 Apr. 1986.
Chemical Abstracts 105: 172,447d Abstract of Jpn Kokai Tokkyo Koho JP 61/68,479 8 Apr. 1986.
P. Benko et al., J. Prakt. Chem. 313 (1) 179 (1971); Chem. Abstr. 75: 129630h (1971).

*Primary Examiner*—Mukund J. Shah
*Assistant Examiner*—Matthew V. Grumbling
*Attorney, Agent, or Firm*—George M. Gould; George W. Johnston; Mark E. Waddell

[57] ABSTRACT

Novel substituted heterocyclic formamidines are useful as ultraviolet light absorbers, the formamidines having the formula

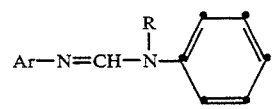

wherein:

Ar represents a 2-thiazolyl, 2-pyridyl, 2- 4,6-dimethyl) pyrmidyl or a 4-(2-methyl)quinolyl group, and, R represents a phenyl group or an alkyl group of from one to eight carbon atoms.

10 Claims, No Drawings

HETEROCYCLIC FORMAMIDINES USEFUL AS ULTRAVIOLET LIGHT ABSORBERS

This application is a division of application Ser. No. 07/630,467 filed Dec. 19, 1990 now U.S. Pat. No. 5,243,055.

BACKGROUND OF THE INVENTION

1. Field of the Invention

This invention discloses novel ultraviolet absorbing heterocyclic formamidines useful for protecting materials against the degradative effects of ultraviolet light.

2. Background Art

Various polymers, plastics, resins, cosmetics, dyes, pigments, lacquers, varnishes, textiles, etc., which are subject to photodegradation by UV-radiation, can be protected by incorporating therein suitable UV-light absorbing agents which will absorb the harmful rays and convert them to relatively harmless forms of energy. To be effective, the light absorbing agent must absorb light efficiently in the ultraviolet portion of the sun's rays which reach the earth, i.e., the range of 280 to 400 nanometers. The agent should also be stable to UV-radiation, compatible with and stable in the medium in which it is incorporated, possess little or no color, be non-toxic, thermally stable, and have low volatility.

The prior art does not teach the novel heterocyclic formamidines of this invention nor their use as valuable UV-light absorbing agents.

SUMMARY OF THE INVENTION

In accordance with the present invention, there are provided heterocyclic formamidines of the formula

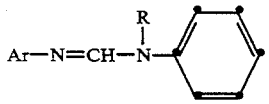

wherein:
- Ar represents a 2-thiazolyl, 2-pyridyl, 2-(4,6-dimethyl) pyrimidyl or a 4-(2-methyl)quinolyl group, and,
- R represents a phenyl group or an alkyl group containing one to eight carbon atoms.

The formamidines of this invention are particularly valuable in as much as they absorb radiation in both the UV-A and UV-B regions, particularly in the range of 280 to 350 nanometers, and are highly resistant to photodegradation. They are colorless at the concentrations used, which makes them particularly valuable in retarding photodegradation in those cases where color could be a problem, such as in clear plastics. They are soluble in most common organic solvents, which facilitates their incorporation into a variety of substrates. They are stable to thermal degradation, which makes them particularly useful in applications where high temperatures are required as, for example, in the molding of plastics.

DESCRIPTION OF THE PREFERRED EMBODIMENTS

As indicated above, the novel formamidines of this invention have the formula

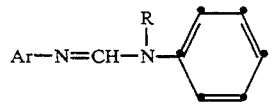

wherein:
- Ar represents a 2-thiazolyl, 2-pyridyl, 2-(4,6-dimethyl)pyrimidyl or a 4-(2-methyl)quinolyl group and,
- R represents a phenyl group or an alkyl group containing one to eight carbon atoms.

Those compounds wherein R represents a phenyl group or an alkyl group containing one to four carbon atoms are the easiest to synthesize and are preferred for that reason. Especially preferred are those compounds wherein R is a phenyl, methyl or ethyl group.

While the phenyl group in formula I (or phenyl groups when R is phenyl) is (are) disclosed as unsubstituted herein, substituted phenyl groups would also be suitable, such phenyl groups having one or more substituents such as carboalkoxy, alkoxy, alkyl, dimethylamino, halogen and the like. The controlling factor in choosing one substituted phenyl over another would, in most cases, be the cost of the starting material needed to prepare the formamidine.

The heterocyclic formamidines of the present invention are prepared in a number of ways, the method chosen being dependent upon the starting material available. One preferred method (Scheme I) involves the reaction of a heterocyclic amine of structure II with a substituted formamide of structure III in the presence of a suitable activating agent such as phosphorus oxychloride, wherein Ar and R are as defined previously.

SCHEME I

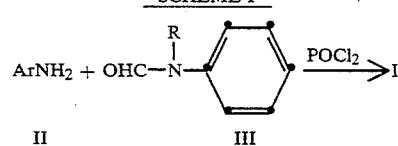

The reaction is effected by adding amine II to a mixture of III and the appropriate activating agent at elevated temperatures. The preferred temperature range is 60°–65° C., and a preferred solvent is toluene. The addition of from 5 to 10% of amine II to the reaction mixture prior to addition of the activating agent appears to enhance the product yields and purities, and is generally preferred.

Another preferred method for preparing the novel formamidines of this invention (Scheme II) involves the reaction of heterocyclic alkyl formimidates IV with substituted anilines V at elevated temperatures, wherein Ar and R are as defined previously, and $R_2$ is an alkyl group of from one to four carbon atoms.

SCHEME II

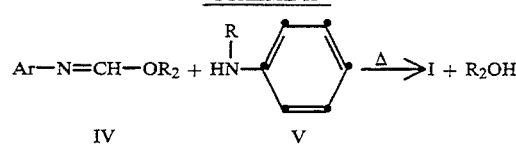

The reaction is effected by heating the reactants from 80° to 250° C.; the preferred temperature range is 120° to 190° C. The preferred procedure is to remove the alcohol which is formed during the reaction and slopping the reaction when no more alcohol is produced. II is especially preferred to use those formimidates wherein $R_2$ is methyl or ethyl.

The strong ultraviolet light-absorbing properties of the formamidines of this invention are demonstrated by dissolving the compounds in isopropanol and determining their spectrum using a recording ultraviolet spectrophotometer. Table I lists the wavelengths of maximum absorption (λ max), the intensity of this absorption calculated as molar extinction coefficient (ε), and the λ range where ε=5,000 or greater.

TABLE I

| COMPOUND | SCHEME | NAME | λmax (nm) | εmax | λRANGE (nm)* |
|---|---|---|---|---|---|
| 1 | I | N'-(2-THIAZOLYL)-N-METHYL-N-PHENYLFORMAMIDINE | 320 | 20,800 | 280–359 |
| 2 | I | N'-(2-THIAZOYL)-N-ETHYL-N-PHENYLFORMAMIDINE | 318 | 20,500 | 280–358 |
| 3 | I | N'-(2-PYRIDYL)-N-METHYL-N-PHENYLFORMAMIDINE | 314 | 17,300 | 280–346 |
| 4 | I | N'-(2-PYRIDYL)-N-ETHYL-N-PHENYLFORMAMIDINE | 314 | 18,200 | 280–345 |
| 5 | II | N'-(2-PYRIDYL)-N-n-OCTYL-N-PHENYLFORMAMIDINE | 314 | 18,800 | 280–348 |
| 6 | II | N'-(2-PYRIDYL)-N,N-DIPHENYLFORMAMIDINE | 318 | 16,700 | 280–349 |
| 7 | II | N'-(2-(4,6-DIMETHYL)-PYRIMIDYL)-N-METHYL-N-PHENYLFORMAMIDINE | 314 | 29,600 | 280–349 |
| 8 | II | N'(4-(2-METHYL)QUINOLYL)-N-METHYL-N-PHENYL-FORMAMIDINE | 323 | 20,000 | 280–350 |

*only wavelengths above 280 nm are included.

All of the formamidines set forth in Table I can be characterized by their high absorptivity and the broad range over which the absorptivity is effective. High absorption over a broad range is an especially desirable property of a commercial UV-screening agent since, in practice, it is often difficult to determine the particular wavelengths of light which can be most deleterious to any material to be protected.

The formamidines of Table I all show excellent photostability in accelerated irradiation tests conducted on isopropanol solutions of the compounds. The formamidines also show excellent resistance to thermal degradation.

Sensitive materials can be protected from the harmful effects of UV-light by incorporating a heterocyclic formamidine of this invention into the UV-sensitive material or into materials used to coat or protect UV-sensitive materials. They can be admixed with dyes or cosmetics to preserve the integrity of these materials. Incorporation into plastics prevents discoloration of the plastic, which may occur in the absence of an effective UV-absorber. They may also be incorporated into plastic containers or container coatings which will serve to protect the contents of such containers from the harmful effects of UV-radiation. They can also be incorporated into compositions used to protect hair, skin and fabric from the deleterious effects of the sun.

The effective amount of screening agent necessary for each application would be dependent on that application and determinable by those skilled in the art. A suitable range is one of about 0.01 wt percent to about 10.0 wt percent. For most applications used to protect UV-sensitive materials, a preferred range of 0.01 wt percent to 4 wt percent is effective, with 0.05 wt percent to 2 wt percent being especially preferred. However, in special formulations where higher concentrations are needed, amounts as high as 10 wt percent may be used.

Higher amounts are often required in cosmetic formulations and compositions used to protect hair and skin. In topical preparations for protection of the skin, it is preferred to use the agent in a range from about 2 wt percent to about 10 wt percent. In skin care preparations and compositions for protection of hair, a preferred range is from about 0.1 wt percent to about 5 wt percent.

ILLUSTRATION OF THE PREFERRED EMBODIMENTS

The following examples provide a more detailed explanation of the invention and are intended as illustrations and not limitations to the invention. Reported melting points were determined in open-ended capillary tubes and are not corrected; 300 MHz, $^1$H-NMR chemical shifts are reported down-field from internal tetramethylsilane (TMS) on the δ scale in ppm; and IR absorptions are reported in reciprocal centimeters.

EXAMPLE 1 (Scheme I)

Preparation of N'-(2-THIAZOLYL)-N-METHYL-N-PHENYL-FORMAMIDINE, 1.

To a stirred suspension of N-methylformanilide (67.6 g; 0.50 mole), toluene (25 g) and 2-aminothiazole (2.0 g; 0.02 mole) was added phosphorus oxychloride (45.8 mL; 0.50 mole) over 15 minutes. The temperature was maintained below 45° C. during this addition. Stirring was continued for 10 minutes, after which time a hot solution of 2-aminothiazole (48.0 g; 0.48 mole) in toluene (250 g) was added at 60°–65° C. over 45 minutes. The reaction was allowed to cool to room temperature with stirring and was quenched by dropwise addition into a mixture of 30% sodium hydroxide (325 g) and ice (300 g). The organic phase was washed with a mixture of water (100 g), sodium chloride (10 g), and sodium bicarbonate (7.5 g), followed by a saturated solution of sodium chloride (125 g); the resultant organic layer was dried over anhydrous magnesium sulfate, filtered, and concentrated to yield 98.3 g of crude product. Vacuum distillation gave pure 1 (60.0 g; 55.3%) as a yellow oil: bp 177° C. @ 0.5 mm Hg. $^1$H-NMR (CDCl$_3$) 8.72 (S, 1H), 7.4–6.9 (m, 7H), 3.50 (S, 3H); IR(neat) 3075, 2950, 1615, 1580, 1490, 1345, 1310, 1120; MS (m/e) 217 (M+, base).

EXAMPLE 2 (Scheme I)
Preparation of N'-(2-THIAZOLYL)-N-ETHYL-N-PHENYLFORMAMIDINE, 2.

Prepared following the procedure of Example 1 from N-ethylformamilide and 2-aminothiazole. Vacuum distillation of the crude product gave pure 2 as a yellow oil: bp 182°–183° C. @ 0.5 mm Hg. ¹H-NMR (CDCl₃) 8.59 (S, 1H), 7.4–6.8 (m, 7H), 4.08 (q, 2H, J=7 Hz), 1.26 (t, 3H, J=7 Hz); IR(neat) 3075, 2980, 1610, 1580, 1490, 1390, 1340, 1130; MS (m/e) 231 (M+, base).

EXAMPLE 3 (Scheme I)
Preparation of N'-(2-PYRIDYL)-N-METHYL-N-PHENYLFORMAMIDINE, 3.

Prepared following the procedure of Example 1 from N-methylformanilide and 2-aminopyridine. Vacuum distillation of the crude product gave pure 3 as a pale yellow oil: bp 164°–165° C. @ 0.5 mm Hg. ¹H-NMR (CDCl₃) 8.94 (S, 1H), 8.30 (d, 1H, J=5 Hz), 7.6–6.9 (m, 8H), 3.52 (S, 3H); IR(neat) 3045, 1620, 1580, 1555, 1500, 1460, 1435, 1235; MS (m/e) 211 (M+), 106 (base).

EXAMPLE 4 (Scheme I)
Preparation of N'-(2-PYRIDYL)-N-ETHYL-N-PHENYLFORMAMIDINE, 4.

Prepared following the procedure of Example 1 from N-ethylformanilide and 2-aminopyridine. Vacuum distillation of the crude product gave pure 4 as a pale yellow oil: bp 164° C. @ 0.5 mm Hg. ¹H-NMR (CDCl₃) 8.83 (S, 1H), 8.30 (m, 1H), 7.5–6.9 (m, 8H), 4.09 (q, 2H, J=7 Hz) 1.26 (t, 3H, J=7 Hz); IR(neat) 2990, 1620, 1570, 1500, 1460, 1440, 1390, 1230, 1130; MS (m/e) 225 (M+), 78 (base).

EXAMPLE 5 (Scheme II)
Preparation of N'-(2-PYRIDYL)-N-n-OCTYL-N-PHENYLFORMAMIDINE, 5.

A mixture of ethyl 2-pyridylformimidate (30.0 g; 0.2 mole) and N-n-octylamine (41.0 g; 0.2 mole) was heated at 180° C. until evolution of ethanol ceased (2.5 hrs.). Vacuum distillation of the residue (62.0 g) gave pure 5 (41.5 g; 67.2%) as a pale yellow oil: bp 215°–217° C. @ 2.0 mm Hg. ¹H-NMR (CDCl₃) 8.80 (S, 1H), 8.29 (m, 1H), 7.5–6.9 (m, 8H), 4.06 (t, 2H, J=7 Hz) 1.70 (m, 2H) 1.3–1.2 (m, 10H), 0.86 (t, 3H, J=7 Hz); IR(neat) 2930, 2860, 1620, 1580, 1555, 1500, 1460, 1230, MS (m/e) 309 (M++1), 94 (base).

EXAMPLE 6 (Scheme II)
Preparation of N'-(2-PYRIDYL)-N,N-DIPHENYLFORMAMIDINE, 6.

Prepared following the procedure of Example 5 from ethyl 2-pyridylformimidate and N,N-diphenylamine. The crude product was recrystallized from a mixture of toluene and petroleum ether to yield pure 6 as pale yellow crystals: mp 92°–94° C. ¹H-NMR (CDCl₃) 9.01 (S, 1H), 8.31 (m, 1H), 7.5–6.9 (m, 13H); IR (CHCl₃) 3060, 3010, 1620, 1580, 1550, 1495, 1460, 1435, 1350, 1230; MS (m/e) 273 (M+), 78 (base).

EXAMPLE 7 (Scheme II)
Preparation of N'-(2-(4,6-DIMETHYL)PYRIMIDYL)-N-METHYL-N-PHENYLFORMAMIDINE, 7.

Prepared following the procedure of Example 5 from ethyl 2-(4,6-dimethyl)pyrimidylformimidate and N-methylaniline. The crude product was recrystallized from a mixture of toluene and petroleum ether to yield pure 7 as off-white crystals: mp 85°–87° C. ¹H-NMR (CDCl₃) 8.98 (S, 1H), 7.4–7.2 (m, 5H), 6.67 (S, 1H), 3.56 (S, 3H), 2.60 (S, 3H), 2.43 (S, 3H); IR (CHCl₃) 3020, 2970, 1570, 1535, 1500, 1350, 1220, 760; MS (m/e) 240 (M+), 42 (base).

EXAMPLE 8 (Scheme II)
Preparation of N'-(4-(2-METHYL)QUINOLYL)-N-METHYL-N-PHENYLFORMAMIDINE, 8.

Prepared following the procedure of Example 5 from ethyl N-(4-(2-methyl)quinolyl)formidate and N-methylaniline. The crude product was recrystallized from hexane to yield pure 8 as pale yellow crystals: mp 126°–127° C. ¹H-NMR (CDCl₃) 2.22 (S, 3H), 3.18 (S, 3H), 6.22 (S, 1H), 6.60–8.0 (m,10H); IR (KBr pellet) 2900, 1570, 1490, 1350, 1315, 1120, 970, 760.

We claim:
1. A compound of the formula

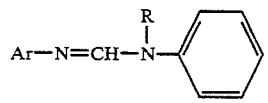

wherein:
Ar represents a 2-pyridyl, 2-(4,6dimethyl)pyrimidyl or a 4,6-dimethyl)pyrimidyl or a 4-(2-methyl)-quinolyl group, and,
R represents a phenyl group or an alkyl group of from one to eight carbon atoms.

2. A compound according to claim 1 wherein the alkyl group is from one to four carbon atoms.

3. A compound according to claim 2 wherein the alkyl group is methyl or ethyl.

4. An ultraviolet-absorbing composition comprising an effective ultraviolet absorbing amount of a compound of the formula

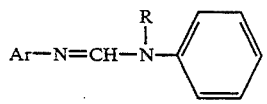

wherein:
Ar represents a 2-pyridyl, 2-(4,6-dimethyl)pyrimidyl or a 4-(2-methyl)quinolyl group, and,
R represents a phenyl group or an alkyl group of from one to eight carbon atoms;
and at least one organic material subject to degradation by ultraviolet light.

5. A method for protecting a first organic compound, subject to degradation by ultraviolet light, with a second organic compound of the formula

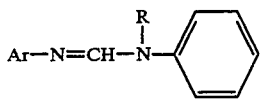

wherein:
Ar represents a 2-pyridyl, 2-(4,6-dimethyl)pyrimidyl or a 4-(2-methyl)quinolyl group, and,
R represents a phenyl group or an alkyl group of from one to eight carbon atoms,
comprising preparing a light screening composition according to claim 1 by contacting an effective ultraviolet absorbing amount of the second organic compound with the first organic material.

6. The compound according to claim 3 wherein Ar represents a 2-pyridyl group and R represents a methyl group.

7. The compound according to claim 3 wherein Ar represents a 2-pyridyl group and R represents an ethyl group.

8. The compound according to claim 3 wherein Ar represents a 2-(4,6-dimethyl)pyrimidyl group and R represents a methyl group.

9. The compound according to claim 3 wherein Ar represents a 2-pyridyl group and R represents a phenyl group.

10. The compound according to claim 3 wherein Ar represents a 4-(2-methyl)quinolyl group and R represents a methyl group.

* * * * *

UNITED STATES PATENT AND TRADEMARK OFFICE
CERTIFICATE OF CORRECTION

PATENT NO. : 5,436,338
DATED : July 25, 1995
INVENTOR(S) : Joseph A. Virgilio, Emanuel Heilweil and Isaac D. Cohen It is certified that error appears in the above-indentified patent and that said Letters Patent is hereby corrected as shown below:

Claim 1, column 6, line 40,
delete "4,6" and insert "4,6-"

Claim 1, column 6, line 41,
delete "or a 4,6-dimethyl)pyrimidyl".

Claim 5, column 7, line 14,
delete "claim 1" and insert "claim 4".

Signed and Sealed this

Thirty-first Day of October 1995

Attest:

BRUCE LEHMAN

Attesting Officer

Commissioner of Patents and Trademarks